United States Patent [19]
Weatherly

[11] Patent Number: 4,911,158
[45] Date of Patent: Mar. 27, 1990

[54] LENS FOLDING BLOCK

[75] Inventor: Gilbert L. Weatherly, Solana Beach, Calif.

[73] Assignee: SKIA International Incorporated, Calif.

[21] Appl. No.: 344,263

[22] Filed: Apr. 27, 1989

[51] Int. Cl.⁴ .......................... A61B 17/00; A61F 2/16
[52] U.S. Cl. ........................................... 606/107; 623/6
[58] Field of Search ................ 128/303 R, 321; 623/6

[56] References Cited

U.S. PATENT DOCUMENTS

| | | | |
|---|---|---|---|
| 4,681,102 | 7/1987 | Bartell | 128/303 R |
| 4,747,404 | 5/1988 | Jampel et al. | 128/303 R |
| 4,759,359 | 7/1988 | Willis et al. | 128/303 R |
| 4,785,810 | 11/1988 | Baccala et al. | 128/303 R X |
| 4,819,631 | 4/1989 | Poley | 128/303 R |

OTHER PUBLICATIONS

*Ophthalmology Times*, May 1, 1988, article on p. 4,33.
*Ophthalmology Times*, Aug. 1, 1988.
*Ophthalmology Times*, May 1, 1988, p. 47.
*Ocular Surgery News*, Jun. 15, 1988, p. 25.
Flyer: Faulkner Titanium Flyer: Katena Memo.

*Primary Examiner*—Ronald L. Frinks
*Attorney, Agent, or Firm*—Cahill, Sutton & Thomas

[57] ABSTRACT

A centrally apertured vertically slidable pedestal supports a foldable intraocular lens implant in predetermined orientation. A blade tipped arm, axially oriented with respect to the pedestal, is protrudable from within the pedestal in diametric orientation with the supported intraocular lens implant upon downward movement of the pedestal. By contacting diametrically opposed sides of the intraocular lens implant with the jaws of forceps followed by downward movement of the pedestal to protrude the blade tip of the arm, the intraocular lens implant becomes folded within the grasp of the forceps and ready for implantation.

21 Claims, 1 Drawing Sheet

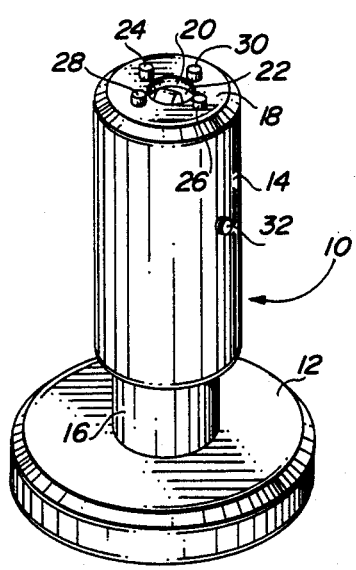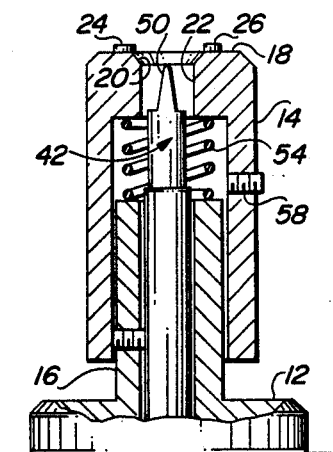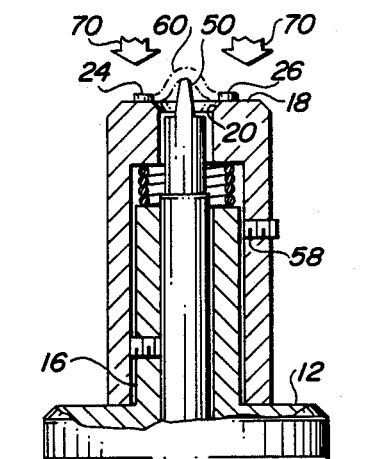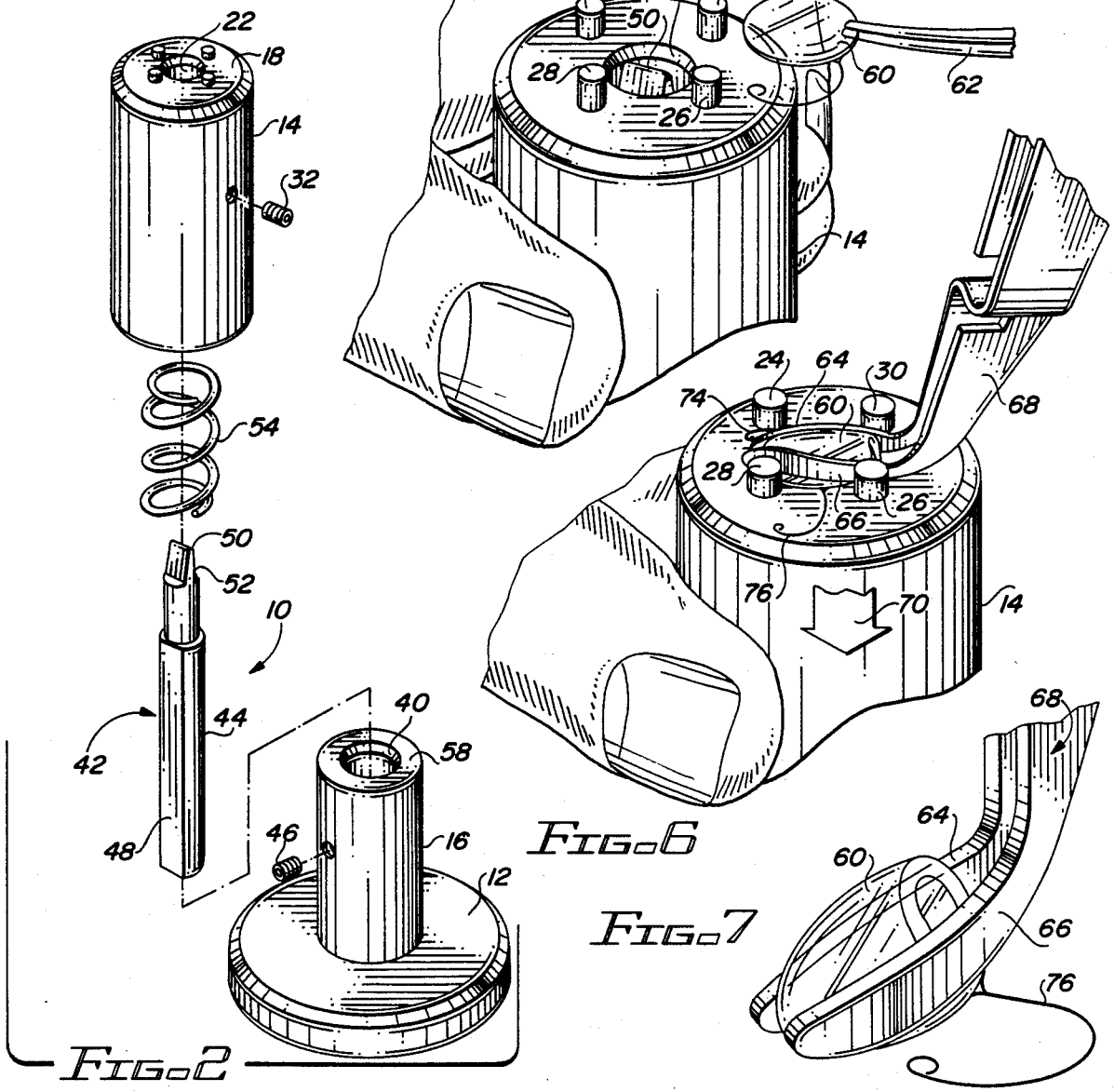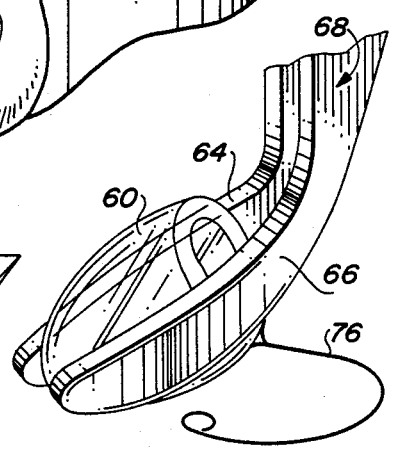

LENS FOLDING BLOCK

BACKGROUND OF THE INVENTION

1. Field of the Invention

The present invention relates to medical implements and, more particularly, to a device for assisting in folding a foldable intraocular lens implant within forceps prior to implantation.

2. Description of the Prior Art

Intraocular lenses of various configurations, with respect to both the lens itself and the haptics, have been developed for many years. Until recently, these lenses required an incision approximately equal in length to the diameter of the lens to be implanted. For a number of medical and clinical reasons, the length of the incision should be kept as short as possible. Through developments in plastic and other materials and by experimenting with such materials to develop intraocular lens implants, a foldable intraocular lens implant has been developed. Various configurations of such foldable implants exist and the materials used therefor vary.

The foldable intraocular lens implant permits the incision during implantation to be relatively substantially shorter than that required for previous implantation procedures. Depending upon the particular procedure used by an ophthalmologist and the particular configuration of the foldable intraocular lens implant, it may be generally stated that the incision with a foldable intraocular lens implant is approximately half the length of an incision for an equivalent diameter intraocular lens implant which is not foldable. The resulting benefits of using a shorter incision without jeopardizing the quality of the intraocular lens implant or attendant surgical procedures suggests that more and more implant procedures will involve foldable intraocular lens implants.

Various techniques have been developed for folding an intraocular lens implant prior to implantation. These procedures generally involve the use of forceps to grip the implant while a further forceps holds the implant diametrically. Many variations on this procedure have been developed by different ophthalmologists commensurate with their particular manual dexterity, surgical skills and preference of instruments.

To assist an ophthalmologist in inserting a folded intraocular lens, devices resembling a tubular or sleeve structure have been developed. The intraocular lens to be implanted is folded and loaded into the device. Thereafter, the folded intraocular lens is expelled from the device into the capsular bag of the eye. A further procedure is necessary to insure correct unfolding and positioning of the unfolded intraocular lens implant within the capsular bag. Such a device provides an effective delivery mechanism but may create medical problems during unfolding upon release from the device.

SUMMARY OF THE INVENTION

A block or pedestal includes a central passageway sized generally commensurate with a foldable intraocular lens to be implanted. An arm having a blade like tip is protrudable from within the passageway past the plane of the lens supporting surface of the pedestal. A spring bias maintains the arm retracted to permit positioning of the foldable intraocular lens upon the pedestal in overlying relationship with the opening to the passageway. Upon protrusion of the arm, it will exert a diametrically oriented upward force upon the overlying intraocular lens. By holding down with forceps opposed edges of the intraocular lens implant, the force exerted by the protruding tip will tend to fold the lens between the jaws of the forceps. Accordingly, the foldable intraocular lens will become foldingly retained by the forceps and ready for implantation.

It is therefore a primary object of the present invention to provide a device for assisting in the folding of a foldable intraocular lens implant between the jaws of forceps prior to implantation procedure.

Another object of the present invention is to provide a device for assisting in positioning a foldable intraocular lens implant within the jaws of forceps.

Yet another object of the present invention is to provide a device for folding an intraocular lens implant, which device may be sterilized by any of standard procedures.

A further object of the present invention is to provide a device for supporting a foldable intraocular lens implant in a predetermined relationship to a fold producing element for folding the intraocular lens implant.

A still further object of the present invention is to provide a relatively mechanically simple and easy to use device for folding a foldable intraocular lens implant between the jaws of forceps.

A still further object of the present invention is to provide a pedestal for supporting a foldable intraocular lens implant and a selectively protrudable element for defining a diametric fold line about which the intraocular lens implant may be folded.

A yet further object of the present invention is to provide a method for folding a foldable intraocular lens implant prior to implantation.

These and other objects of the present invention will become apparent to those skilled in the art as the description thereof proceeds.

BRIEF DESCRIPTION OF THE DRAWINGS

The present invention will be described with greater clarity and specificity with reference to the following drawings, in which:

FIG. 1 illustrates a lens folding block prior to use;

FIG. 2 illustrates an exploded view of the major components of the lens folding block;

FIG. 3 is a cross sectional view illustrating the lens folding block prior to use;

FIG. 4 is a cross sectional view illustrating the lens folding block in position for folding an intraocular lens implant;

FIG. 5 illustrates the first step in effecting folding of an intraocular lens implant;

FIG. 6 illustrates a second step in folding an intraocular lens implant; and

FIG. 7 illustrates a folded intraocular lens implant lodged between the jaws of forceps.

DESCRIPTION OF THE PREFERRED EMBODIMENT

Referring to FIG. 1, there is shown a lens folding block 10 usable to assist in folding a foldable intraocular lens implant between the jaws of insertion forceps or part of an implantation procedure. The block includes a base 12 for supporting a vertically translatable pedestal 14. A column 16, extending upwardly from base 12, axially guides the pedestal. Top surface 18 of pedestal 14 is centrally apertured with aperture 20. The aperture defines entry to a passageway 22 extending through the pedestal. A pair of diametrically opposed studs 24,26 protrude upwardly from surface 18. These studs are used primarily for positioning and locating purposes related to placement of a foldable intraocular lens implant upon the top surface and to the positioning of the jaws of forceps relative to the intraocular lens implant. Under certain circumstances, a second pair of diametrically opposed studs 28,30 may be employed to extend from surface 18. A set screw 32, or the like, may be employed to lock pedestal 14 in place during storage and transport.

Referring to FIG. 2, certain further details of lens folding block 10 will be described. Column 16 may include a cavity 40, which cavity is axially disposed therein. An arm 42 includes a lower shaft part 44 for insertion within cavity 40. A set screw 46, or the like, threadedly and penetrably engages the wall of column 16 to lockingly engage flat 48 attendant shaft 44. Accordingly, set screw 46 maintains arm 42 in fixed relationship to column 16 and prevents rotation of the arm relative to the column. The upper end of arm 42 includes a blade 50 formed by a tapered end 52. A coil spring 54, or the like, bears against a shoulder 56 (See FIGS. 3 and 4) within pedestal 14 and against the upper end 58 of column 16 to bias or urge the pedestal upwardly with respect to the column.

Pedestal 14 penetrably engages arm 42 by insertion of the arm within passageway 22. The longitudinal dimension of arm 42 commensurate with the length of pedestal 14 locates the tip of blade 50 at or below the plane defined by top surface 18 when the pedestal is in its extended position under urging of coil spring 54. Thus, the coil spring 54 serves as a means for discouraging protrusion of the tip of blade 50 through aperture 20 and urges the pedestal away from the tip. Upon downward movement of the pedestal relative to arm 42, blade 50 will protrude through aperture 20 and extend a predetermined distance above top surface 18. Set screw 32, penetrably and threadedly engaging the side wall of pedestal 14, frictionally engages either the arm or the column (depending on its physical location) to restrict relative movement between the pedestal and the arm. The set screw may be used to prevent such relative movement during storage and/or transport of lens folding block 10. Alternatively, it may be used to limit the extent of translation of pedestal 14 relative to arm 42 to control the extent of protrusion of blade 50 above top surface 18.

Referring jointly to FIGS. 3 to 7, the steps of folding a foldable intraocular lens implant will be described. In the initial position depicted in FIG. 3, pedestal 14 is in its extended state. In this state, blade 50 is disposed within passageway 22 and below the plane defined by top surface 18. A foldable intraocular lens implant 60 to be folded is placed upon top surface 18 by use of forceps 62, or the like. As discussed above, although four studs 24,26,28 and 30 are shown, these studs are used for orientation purposes and adequate orientation may be obtained from a single pair of opposed studs.

After placement of intraocular lens implant 60 upon platform 18 in overlapping concentric relationship with aperture 20, jaws 64,66 of forceps 68 are placed upon diametrically opposed edges of lens 60, as illustrated in FIG. 6. As illustrated, studs 24,26,28 and 30 may be employed by the ophthalmologist to assist him in orienting and positioning the jaws of forceps 68 with respect to diametrically opposed edges of the intraocular lens implant. Clearly, the studs are not required for this purpose but may be employed in the manner of aids to positioning accuracy.

After engagement of the jaws of forceps 68 with intraocular lens implant 60, pedestal 14 is translated downwardly, as representatively depicted by arrows 70 shown in FIGS. 4 and 6. The downward movement of the pedestal will result in protrusion of blade 50 past aperture 20 and past the plane represented by top surface 18, as depicted in FIG. 4. The protruding blade will diametrically engage intraocular lens implant 60. The resulting force exerted upon the intraocular lens implant by the blade in combination with the anchoring of opposed edges of the intraocular lens implant by the jaws of the forceps at surface 18 will result in folding of the intraocular lens implant. Commensurate with such folding of the intraocular lens implant, the forceps can be slightly squeezed to bring the diametrically opposed halves of the intraocular lens toward one another and generally adjacent opposed sides of blade 50.

Once intraocular lens implant 60 becomes disposed in its folded state intermediate jaws 64,66 of forceps 68, pedestal 14 may be raised to withdraw blade 50 from within the folded intraocular lens implant. Commensurate with withdrawal of the blade, the jaws of the forceps will tend to urge the opposed halves of the folded intraocular lens implant toward one another and into the configuration illustrated in FIG. 7. Depending upon the type of intraocular lens implant employed, haptics 74,76 extending from the intraocular lens implant and used to centrate the intraocular lens implant within the capsular bag of the eye, may be left freely extending, as illustrated. Alternatively, they may be bent and temporarily positionally retained within the fold of the intraocular lens.

As represented by the depiction of a thumb and fingers in FIGS. 5 and 6, it is intended that pedestal 14 be translated relative to arm 42 by the ophthalmologist performing the implant procedure or by one of his medical staff. The downward translation of pedestal 14 is an easy to perform maneuver requiring little attention and it is a reasonably foolproof method for protruding blade 50 to bring about folding of the intraocular lens implant.

It is to be understood that arm 42 may be relocated relative to pedestal 14 by means of a protruding lever, prong or other directly or indirectly connected mechanism. Such structure would, however, complicate the operation of the device and would appear to be unwieldy in an operating room atmosphere. That is, in the illustrated configuration of lens folding block 10, the act of downwardly translating the pedestal simultaneously stabilizes the lens folding block against unwanted motion while accomplishing the step of providing assistance in the process of folding a foldable intraocular lens implant prior to an implant procedure.

While the principles of the invention have now been made clear in an illustrative embodiment, there will be immediately obvious to those skilled in the art many modifications of structure, arrangement, proportions, elements, materials and components used in the practice of the invention which are particularly adapted for specific environments and operating requirements without departing from those principles.

I claim:

1. A lens folding block for assisting in the folding of a foldable intraocular lens implant upon placement of the jaws of forceps upon opposed edges of the intraocular lens implant, said lens folding block comprising in combination:

(a) a base;

(b) an arm extending from said base, said arm including a tip for diametrically contacting the intraocular lens implant;

(c) a pedestal for supporting the intraocular lens implant; and (d) means for protruding said tip with respect to said pedestal into contact with the intraocular lens implant to urge upward movement of the intraocular lens implant along a diametric line and resulting in folding of the intraocular lens implant intermediate the jaws of the forceps.

2. The lens folding block as set forth in claim 1 wherein said pedestal includes a passageway for translatably receiving said arm.

3. The lens folding block as set forth in claim 2 wherein said pedestal includes a top surface having an aperture for defining the upper opening of said passageway through which said tip is protrudable.

4. The lens folding block as set forth in claim 3 including at least a pair of studs disposed radially outwardly of said opening and extending from said top surface for guiding the placement of the intraocular lens implant and the jaws of the forceps.

5. The lens folding block as set forth in claim 1 including means for discouraging protrusion of said tip.

6. The lens folding block as set forth in claim 5 wherein said pedestal is translatably mounted with respect to said arm.

7. The lens folding block as set forth in claim 6 wherein said discouraging means urges said pedestal away from said tip.

8. The lens folding block as set forth in claim 1 including a column extending from said base for supporting said arm.

9. The lens folding block as set forth in claim 8 including means for translating said pedestal and juxtaposed with respect to said column and said arm.

10. The lens folding block as set forth in claim 9 including means for biasing said pedestal away from said tip.

11. The lens folding block as set forth in claim 1 wherein said tip includes a tapered section at the extremity of said arm.

12. The lens folding block as set forth in claim 11 wherein said tapered section defines a blade.

13. A method for assisting the folding of a foldable intraocular lens implant between the jaws of forceps, said method comprising the steps of:

(a) placing an intraocular lens implant upon the top surface of a pedestal with a passageway disposed in the pedestal;

(b) engaging opposed sides of an intraocular lens implant with the jaws of the forceps;

(c) forcing the intraocular lens implant upwardly between the engaged sides and along a generally diametric line; and (d) folding the intraocular lens implant between the jaws of the forceps by squeezing the jaws of the forceps in combination with exercise of said step of forcing.

14. The method as set forth in claim 13 wherein said step of forcing includes the step of protruding a tip from the pedestal.

15. The method as set forth in claim 14 including the step of discouraging said step of protruding.

16. The method as set forth in claim 13 including the step of terminating exercise of said step of forcing.

17. The method as set forth in claim 13 including the step of resisting exercise of said step of forcing during exercise of said step of placing.

18. The method as set forth in claim 17 wherein said step of forcing includes the step of translating a blade disposed within the passageway relative to the pedestal to protrude the blade from the pedestal.

19. The method as set forth in claim 18 wherein said step of translating includes the step of repositioning the pedestal relative to the blade.

20. The method as set forth in claim 19 wherein the blade extends from an arm and including the step of supporting the arm upon a base.

21. The method as set forth in claim 20 wherein said translating step includes the step of translating the pedestal along the arm.

* * * * *